United States Patent [19]

Best et al.

[11] Patent Number: 5,030,571

[45] Date of Patent: Jul. 9, 1991

[54] RHODOCOCCUS BACTERIUM FOR THE PRODUCTION OF ARYL ACYLAMIDASE

[75] Inventors: David J. Best, Olney; Peter A. Vaughan, Oxon, both of Great Britain

[73] Assignee: Medisense, Inc., Cambridge, Mass.

[21] Appl. No.: 79,759

[22] Filed: Jul. 30, 1987

[30] Foreign Application Priority Data

Jul. 30, 1986 [GB] United Kingdom ................. 8618559

[51] Int. Cl.$^5$ ............................................... C12N 9/78
[52] U.S. Cl. ........................................ 435/227; 435/4; 435/29; 435/18; 435/228; 435/253.2
[58] Field of Search ...................... 435/227, 228, 4, 18, 435/29, 253.2

[56] References Cited

FOREIGN PATENT DOCUMENTS 0053470 6/1982 European Pat. Off. .
0053890 6/1982 European Pat. Off. .
0179523 4/1986 European Pat. Off. .
0184895 6/1986 European Pat. Off. .

OTHER PUBLICATIONS

Stamicarbon–Chem. Abst. vol. 105(1986) pp. 170,617k.
Hammond et al., "Development of an Enzyme-Based Assay for Acetaminophen", Analytical Biochemistry 143:152-157 (1984).
Hammond et al., "Purification and Properties of Aryl Acylamidase from Pseudomonas Fluorescens ATCC 39004", Eur. J. Biochem. 132:651-655 (1983).

*Primary Examiner*—Sam Rosen

[57] ABSTRACT

An aryl acylamidase is produced by a process which comprises culturing in a culture medium an aryl acylamidase-producing bacterial strain selected from *Rhodococcus erythropolis* NCIB 12273 and aryl acylamidase-producing mutants or variants thereof, and collecting aryl acylamidase-containing material.

10 Claims, No Drawings

RHODOCOCCUS BACTERIUM FOR THE PRODUCTION OF ARYL ACYLAMIDASE

The present invention relates to the production of aryl acylamidase enzymes, to microorganisms capable of producing said enzymes, and to an aryl acylamidase enzyme.

The aryl acylamidase enzymes referred to herein are defined by the International Union of Biochemistry (Enzyme Nomenclature 1978, Academic Press, New York) as those enzymes which catalyse the hydrolysis of anilides to anilines plus fatty-acid anions. These enzymes are given the enzyme classification E.C. 3.5.1.13.

Aryl acylamidase enzymes can, for example, hydrolyse acetanilide, acetaminophen (paracetamol; p-hydroxy acetanilide) and phenacetin (p-ethoxyacetanilide), and consequently can be used in methods for the estimation of these and other N-acylated primary aromatic amines, which are used as drugs, such as paracetamol. Rapid estimation is preferred as such drugs are often taken in overdose quantities and prompt and correct medication is required, if the production of toxic metabolic products is to be avoided.

In one such assay method, as described in European Patent Specification No. 53470 (United Kingdom Public Health Laboratory Service Board, Porton Down), the anilide is hydrolysed by the enzyme and the products of hydrolysis are determined spectrophotometrically. Additional details of this method are given in Hammond et al. (1984) "Development of an enzyme-based assay for acetaminophen", Analytical Biochemistry 143: 152–157.

In an alternative method, as described in European Patent Specification No. 184895 (Genetics International Inc.), an electrode poised at a suitable potential is exposed to a sample which is suspected of containing the anilide and which has been treated with the enzyme. The current generated at the electrode is a measure of the quantity of hydrolysis products formed.

Methods of production of the enzymes which catalyse the above-mentioned deacylation have been known for several years. European Patent No. 53890 "Production of aryl acylamidases" (United Kingdom Public Health Laboratory Service Board, Porton Down) mentions several references to sources of the enzyme, including bacteria of genus Pseudomonas and genus Bacillus, as well as moulds of genus Penicillium.

The production of aryl acylamidase enzymes from strains of Pseudomonas is particularly well characterised, and is the subject of the above-mentioned patent, which suggests that enzyme activity is induced during the growth of certain pseudomonads on tryptone soya broth in the presence of an anilide. Additional details of methods for the production of aryl acylamidase are to be found in Hammond et al. (1983) "Purification and properties of Aryl Acylamidase from *Pseudomonas fluorescens* ATCC 39004", European Journal of Biochemistry, 132: 651–655.

The present invention provides a novel process for producing an aryl acylamidase enzyme. The present process comprises culturing bacteria of the strain *Rhodococcus erythropolis* NCIB 12273 or aryl acylamidase producing mutants or variants thereof in a culture medium in which said bacterial strains are capable of producing aryl acylamidase, and collecting the aryl acylamidase enzyme-containing material.

Preferably the cultivation is effected batch-wise at 25° to 35° C. for 10 hr to 40 hr after inoculating in to a growth medium of pH 7 to 8. The enzyme-containing material is typically collected as a cell-free extract, and can be purified by conventional techniques including batch ion exchange, column ion exchange, hydrophobic interaction chromatography, and salt precipitation techniques.

According to a further aspect of the present invention there is provided, the strain *Rhodococcus erythropolis* NCIB 12273 or aryl acylamidase producing mutants or variants thereof.

*Rhodococcus erythropolis*, a Gram-positive strain, belongs to the family Nocardiaceae, of the order Actinomycetales.

Conveniently, the bacterial strain is capable of producing aryl acylamidase when grown in a tryptone soya broth in the presence of an aryl acylamidase inducer, more preferably, acetanilide.

According to a yet further aspect of the present invention there is provided a preparation having an aryl acylamidase activity, obtained from a culture of the strain *Rhodococcus erythropolis* NCIB 12273 or aryl acylamidase producing mutants or variants thereof.

Preferably, the preparation contains dithiothreitol, $\beta$-mercaptoethanol, or other thiol protecting agent, in order to reduce the loss of enzyme activity during storage.

The present invention is illustrated by the following Examples.

EXAMPLE 1

Preliminary Isolation

The *R. erythropolis* strain NCIB 12273 was one of six organisms isolated from garden soil by selective enrichment upon the aromatic amide acetaminophen (paracetamol; p-hydroxyacetanilide) as the sole source of carbon and energy.

A minimal salts medium (50 ml, pH 7.0; (Table 1)), containing acetaminophen (0.1% w/v) as sole source of carbon and energy, was inoculated with a small quantity of garden soil from a flowerbed.

TABLE 1

| Composition of minimal salts medium | |
|---|---|
| | g/l |
| $NaNO_3$ | 0.850 |
| $KH_2PO_4$ | 0.560 |
| $Na_2HPO_4$ | 0.860 |
| $K_2SO_4$ | 0.170 |
| $MgSO_4.7H_2O$ | 0.037 |
| $CaCl_2.2H_2O$ | 0.007 |
| Fe(III)EDTA | 0.004 |
| trace element solution | 2.5 ml/l |
| trace element solution | |
| $ZnSO_4.7H_2O$ | 0.232 |
| $MnSO_4.4H_2O$ | 0.178 |
| $H_3BO_3$ | 0.056 |
| $CuSO_4.5H_2O$ | 0.100 |
| $Na_2MoO_4.2H_2O$ | 0.039 |
| $CoCl_2.6H_2O$ | 0.042 |
| KI | 0.066 |
| EDTA | 0.100 |
| $FeSO_4.7H_2O$ | 0.040 |
| $NiCl_2 6H_2O$ | 0.0004 |
| $H_2SO_4$ (1M) | 8.0 ml |

The initial cultures were incubated for two to five days on an orbital shaker (200 r.p.m.) at 30° C. before undergoing a secondary isolation procedure.

EXAMPLE 2

Secondary Isolation Procedures

The secondary isolation procedure involved direct plating of the initial enrichment and subsequent isolation to purity of organisms arising on the test plates. The enrichments were plated onto minimal salts agar containing acetaminophen at a concentration of 0.1% (w/v).

At the end of these enrichment procedures six pure cultures were isolated. One of these isolates was found to be a gram-positive organism capable of growth upon minimum agar containing either 0.1% acetaminophen or 0.1% phenacetin. Discoloration of the medium occurred in both cases. Medium discoloration was used as an indication of the formation and reaction of substituted anilines, which in turn indicated that the organism was able to hydrolyse the anilide substrate and therefore possessed aryl acylamidase activity. The organism was identified as a strain of *Rhodococcus erythropolis* on the basis of the characteristics given below.

Characteristics of the organism

The isolated organism showed the following morphological and staining characteristics when grown on Nutrient Agar at 30° C.:

Shape: Rod
Motility: Negative
Spores: None
Gram Stain: Positive

The colonies produced after 3 days growth at 30° C. on Nutrient Agar were round, regular, entire, smooth, convex, off-white, shiny, mucoid and opaque, and 2 to 3 mm in diameter.

After 10 days growth at 30° C. the colonies had a pale pink colour.

The organism was catalase positive, oxidase (Kovacs) negative, and weakly oxidative in the O-F glucose test.

The organism showed the following characteristics in 48 hr tests at 25° C.;

| | |
|---|---|
| $NO_3$ reduction, | −ve |
| Indole production, | −ve |
| Acid production from glucose, | −ve |
| Arginine dehydrolase activity, | −ve |
| Urease, | +ve |
| Aesculin hydrolysis, | +ve (weak) |
| Gelatin hydrolysis, | −ve |
| β-galactosidase, | trace |
| Glucose assimilation | +ve |
| Arabinose assimilation, | −ve |
| Mannose assimilation, | −ve |
| Mannitol assimilation, | +ve |
| N-acetylglucosamine assimilation, | +ve |
| Maltose assimilation, | −ve |
| Gluconate assimilation, | +ve |
| Caprate assimilation, | −ve |
| Adipate assimilation, | +ve |
| Malate assimilation, | +ve |
| Citrate assimilation, | +ve |
| Phenylacetate assimilation, | +ve |
| Cytochrome Oxidase | −ve |

The organism showed the following characteristics in 7 day tests at 25° C.;

| | |
|---|---|
| Decomposition of; | |
| Adenine | +ve |
| Tyrosine | +ve |
| Urea | +ve |
| Allantoin | −ve |
| Acid from: | |
| Inositol | +ve |
| Trehalose | +ve |
| Mannitol | +ve |
| Sorbitol | +ve |
| Growth on Sole Carbon Sources: | |
| Glycerol | +ve |
| Sorbitol | +ve |
| Maltose | +ve |
| Trehalose | +ve |
| Benzoate | −ve |
| Citrate | +ve |
| Lactate | +ve |
| L-Tyrosine | −ve |
| p-hydroxybenzoate | +ve |
| Other Characteristics | |
| ONPG | +ve |
| Tween 80 | +ve |
| Colour on glucose agar | pale pink, mucoid |
| Phosphatase | +ve |
| Growth at 10° C. | +ve |
| Growth at 40° C. | −ve |

These characteristics indicated that the organism was a strain of *R. erythropolis*, atypical in not growing at 40° C.

The effects of variations of culture pH and culture temperature on the growth of the strain were examined. The organism will grow throughout the pH range examined, from pH 6.6 to pH 8.4, with an optimum growth rate between pH 7.0 and pH 8.0. A comparison of growth rates at 26°, 30° and 35° C. indicated that the growth was fastest at 30° C.

The strain was deposited under the Budapest Treaty at the National Collection of Industrial Bacteria, at the Torry Research Station, PO Box 31, 135 Abbey Rd Aberdeen, AB9 8DG, England on the 26th of June 1986 and given the accession number NCIB 12273. Samples will be available under the relevant law.

EXAMPLE 3

Extraction of Aryl Acylamidase Activity.

The isolated strain of *R. erythropolis* was grown in 100 ml 2% tryptone soya broth containing 0.1% acetanilide to an $A_{600}$ of 1.8 (all A values quoted in this patent specification were measured on a Cecil model CE 594 spectrophotometer). The culture was harvested by centrifugation (10,000 g 10 minutes) and the pellet was resuspended in Tris/HCl buffer (50 mM, pH 8.6) to be washed. After centrifugation the washed cell pellet was resuspended in 5 ml of the same buffer and the resuspended cell suspension disrupted by ultrasonication (4×30 second bursts, 16 mµ amplitude with 2 minute cooling periods). The disrupted cell suspension was centrifuged (10,000 g, 30 minutes) to remove cellular debris and the supernatant carefully removed and stored on ice to await analysis.

Aryl acylamidase activity was detected by the two following methods.

(1) The discontinuous assay method:

The reaction mixture consisted of the following; cell-free extract (100 µl); acetaminophen (26.5 mM; 100 µl); Tris/HCl buffer (100 mM, pH 8.6, 800 µl). This was thoroughly mixed and incubated at thirty degrees centigrade. After the required elapsed period the reaction was terminated by the addition of the following; o-cresol (1% v/v aqueous solution; 2 ml); copper (II) sulphate (0.2% w/v of the anhydrous salt to which 0.880 ammonia had been added (1.6 ml/100 ml); 0.2 ml); distilled water (1.4 ml). The formation of a blue pigment verified the presence of the reaction product p-aminophenol and this was quantified by measurement of absorbance at 615 nm and comparison with a standard curve prepared with p-aminophenol (Hammond et al., 1984), (2) The continuous assay method:

Reaction mixtures consisted of the following: Tris/HCl buffer (100 mM, pH 8.6; 0.6 ml); p-nitroacetanilide (1 mM, prepared by dissolving the solid in ethanol prior to dilution to give a final ethanol concentration of 10% v/v). The reaction was initiated by the addition of cell-free extract (400 μl) and the reactions incubated at 30° C. The product of the reaction, p-nitroaniline absorbs strongly at 405 nm and under these conditions has a molar extinction coefficient of 10,000 1/mol/cm.

The aryl acylamidase activity of the cell-free extract as measured by the continuous assay method was 0.34 μmol p-nitroacetanilide hydrolysed per min per mg protein.

The continuous assay method was taken as the basis for defining a unit of activity of the enzyme. Specifically, one unit of enzyme activity is defined as 1 μmol of p-nitroacetanilide hydrolysed to p-nitroaniline per minute, under the continuous assay conditions.

EXAMPLE 4

Enzyme Storage

Cell-free extracts of the isolated R. erythropolis strain prepared using 50 mM-Tris/HCl buffer (pH 8.6) lost most of the aryl acylamidase activity when stored for an 18 hr period at 4° C. The stability of the enzyme was greatly improved by the addition of 1 mM dithiothreitol to the extracts. In the presence of 1 mM dithiothreitol only some of the initial aryl acylamidase activity was lost in cell-free extracts after storage at 4° C. for 18 hr.

The protease inhibitor phenylmethylsulphonyl fluoride was also tested for its effect on the stability of aryl acylamidase in cell-free extracts but was found to decrease aryl acylamidase activities relative to controls.

EXAMPLE 5

15 Liter Scale Culture of R. erythropolis

The strain of R. erythropolis was grown in a 20 liter fermenter containing 15 liters of 2% tryptone soya broth plus 0.1% acetanilide (as an aryl acylamidase inducer) plus 0.33% (v/v) polypropylene glycol P2000, at 30° C. and pH 7.2. The fermenter was aerated at 5 liters air per min. The inoculum used was a 500 ml culture grown on the same medium for 32 h. Growth was essentially complete after 24 hours at which time the culture had attained an $A_{600}$ of 7.0. The specific activity of aryl acylamidase measured in cell-free extracts of culture samples was highest in the late exponential phase of growth (after about 18 hrs of growth), when it was 0.59 units per mg protein.

EXAMPLE 6

75 Liter Scale Culture of R. erythropolis

A 250 ml shake flask containing 100 ml 2% tryptone soya broth (Oxoid) plus 0.1% acetanilide (BDH) in deionized water, was loop inoculated from a nutrient agar slant of the R. erythropolis. The culture was grown at 30° C. on an orbital shaker (150 rpm) for 72 h and then 20 ml aliquots were used to inoculate four 2 liter shake flasks each containing 500 ml of the same medium. These cultures were grown for 16 h under the same conditions and then used to inoculate 75 liters of the same medium (plus 0.1% polypropylene glycol P2000) in a 100 liter pilot plant fermenter (Bioengineering, Switzerland). The growth conditions were; temperature 30° C., aeration 25 liters per min, pH 7.2 (maintained by automatic addition of 0.2M HCl). The stirrer speed was 400 rpm. The culture attained an $A_{600}$ of 7.2 after 18 h incubation at which time it was harvested using a Sharples continuous centrifuge to yield 550 g wet weight cells.

EXAMPLE 7

Enzyme Purification Procedures

A culture of R. erythropolis was grown by the method described in Example 5. After 17 h growth the culture had attained an $A_{600}$ of 6 and was harvested using a Sharples continuous centrifuge, 150 g wet weight cells were recovered. The cells were washed by resuspending them in approximately 300 ml 50 mM Tris/HCl pH 7.5 buffer and then centrifuging the suspension at 11,000 g for 90 min at 4° C. to produce a supernatant which was discarded, and a cell pellet. The cell pellet was resuspended to 300 ml in 50 mM Tris/HCl pH 7.5 buffer and the resulting suspension was stored at −20° C. until required.

A1: Batch Ion Exchange Procedure

For the ion exchange purification procedure, 4 g of DE52 ion exchange resin (Whatman), which had been previously equilibrated with 50 mM Tris/HCl pH 7.5 buffer, was added to 56 ml of cell-free extract. The cell-free extract was obtained by taking 60 ml of the harvested suspension stored at −20° C., thawing the suspension, and adding 10 ml 50 mM Tris/HCl pH 7.5 buffer, together with dithiothreitol (DTT) to 1 mM. The suspension was split into two batches each of which were sonicated (10×45 second periods, 16 mμ amplitude with 2 minute cooling periods). The sonicated material was pooled then centrifuged at 31,000 g for 70 min, at 4° C., to yield 57 ml cell-free extract.

The mixture of the cell-free extract and the DE52 resin was stirred at 4° C. for 3 h and then the DE52 resin was allowed to settle out. The supernatant was decanted and the DE52 resin was washed by adding 80 ml 20 mM Tris/HCl pH 7.5 buffer (containing 1 mM DTT) and stirring the suspension for 5 min at 4° C. The DE52 resin was again allowed to settle and the supernatant decanted to leave the ion exchange resin suspended in approximately 4 ml buffer (total volume approximately 7 ml). To this was added 21 ml 20 mM Tris/HCl pH 7.5 containing 0.4M sodium chloride plus 1 mM DTT to produce a final salt concentration of approximately 0.35M. The suspension was stirred for 2 h and then filtered through a 0.4 μm filter to remove the ion exchange resin, the filtrate contained the aryl acylamidase. A 1.8 fold protein purification was achieved, i.e. an increase in the aryl acylamidase specific activity from 0.58 units per mg protein to 1.05 units per mg protein. The recovery of the enzyme was 77%.

A2: Column Ion Exchange Procedure

The material produced by the batch DE52 resin purification procedure was further purified by ion exchange chromatography on a column of Pharmacia Q-Sepharose Fast Flow gel (a cross-linked agarose gel containing quaternary amine functional groups). A 5 ml sample of the DE52 resin purified material was mixed with 1 ml 20 mM Tris/HCl pH 7.5 to dilute the NaCl concentration of the sample to less than 0.3M. A 5 ml volume of the diluted sample was applied to a 48 ml Q-Sepharose column (9×2.6 cm) which had been previously equilibrated with 20 mM Tris/HCl pH 7.5 buffer containing 0.3M NaCl plus 1 mM dithiothreitol (DTT). The protein was eluted with 240 ml of the same buffer followed by 240 ml of 20 mM Tris/HCl pH 7.5 buffer plus 0.4M NaCl (and 1 mM DTT). The flow rate was 240 ml per hour, 10 ml fractions of the eluent were collected. The aryl acylamidase eluted after between 60 and 150 ml of the 0.4M NaCl buffer had been applied to the column. A protein purification of 4.9 fold was achieved with a 90% yield.

A3: Hydrophobic Interaction Chromotagraphy

A sample of enzyme solution produced by the Q-Sepharose column purification procedure was desalted by diafiltration, and concentrated, using an Amicon 30,000 molecular weight cutoff hollow fibre cartridge and 20 mM Tris/HCl pH pH 7.5 buffer containing 1 mM dithreitol (DTT). Further concentration of the sample was achieved using an Amicon ultrafiltration cell fitted with a 30,000 molecular weight cutoff membrane. This procedure resulted in a protein purification of the enzyme of approximately 2 fold.

A 0.5 ml sample of the 0.42 mg protein per ml, 12.5 units aryl acylamidase per mg protein, concentrated solution produced by the above procedure was applied to a 4 ml (2×1.6 cm) column of Pharmacia Phenyl Sepharose gel (a phenyl substituted cross-linked agarose gel) which had been previously equilibrated with 0.5M ammonium sulphate in 20 mM Tris/HCl pH 7.5 plus 1 mM DTT. The column was washed with 10 ml of the same solution and the enzyme eluted with a 20 ml linear descending gradient of 0.5– 0.0M ammonium sulphate in 20 mM Tris/HCl pH 7.5 plus 1 mM DTT, followed by 20 ml of 20 mM Tris/HCl pH 7.5 plus 1 mM DTT. The flow rate was 0.33 ml per min and 1 ml fractions were collected. The enzyme eluted towards the end of the descending ammonium sulphate gradient. A 1.9 fold purification was achieved, i.e. the aryl arcylamidase specific activity was increased from an initial 12.5 units per mg protein to 23.2 units per mg protein, the recovery was 85%.

B: Ammonium Sulphate Precipitation

It was found that most (86%) of the aryl acylamidase in a crude cell-free extract of *R. erythropolis* precipitated between 20 and 40% ammonium sulphate saturation. (The crude cell-free extract contained 10 mg per ml protein and had an aryl acylamidase activity of 0.48 units per mg protein. The extract was in 50 mM Tris/HCl pH 7.0 buffer containing 1 mM ethylenediaminetetracetic acid and 1 mM dithothreitol).

EXAMPLE 8

Other Enzyme Properties

Other properties of the enzyme were investigated.

Using an enzyme which had been purified by a batch ion exchange procedure followed by the column ion exchange procedure, the p-nitroacetanilide assay was used in determination of the effect of pH on the activity of the *R. erythropolis* aryl acylamidase. The enzyme had a broad pH optimum with maximum activity at around pH 8.0.

Using an enzyme sample which had been purified by column ion exchange chromatography and then desalted using a Pharmacia PD-10 gel filtration column, the isoelectric point of the *R. erythropolis* aryl acylamidase was determined by isoelectric focusing gel electrophoresis. The enzyme was visualised on the gel by a p-nitroacetanilide activity stain for aryl acylamidase activity and its position in the pH gradient was determined in relation to coloured protein markers of known isoelectric points. The enzyme focused in a position mid-way between protein markers with isoelectric points of pH 6.45 and pH 7.3, which indicates that the isoelectric point of the *R. erythropolis* aryl acylamidase was approximately pH 7.0.

We claim:

1. A process for producing an aryl acylamidase which process comprises culturing in a culture medium an aryl acylamidase-producing bacterial strain selected from *Rhodococcus erythropolis* NCIB 12273 and aryl acylamidase-producing mutants or variants thereof, and collecting aryl acylamidase-containing material.

2. A process as claimed in claim 1, wherein the aryl acylamidase-containing material is a cell-free extract.

3. A process as claimed in claim 1 or 2, wherein the bacterial strain is cultivated at 25° to 35° C. for 10 to 40 hours after inoculation of a growth medium of pH 7 to 8.

4. A process as claimed in claim 1 or 2, wherein the culture medium contains an aryl acylamidase inducer.

5. A process as claimed in claim 4, wherein the inducer is acetanilide.

6. A method of assay for an N-acylated primary aromatic amine, in which the amine is hydrolysed with an aryl acylamidase produced by a process according to any one of claim 1 or claim 2.

7. The strain *Rhodococcus erythropolis* NCIB 12273 or aryl acylamidase-producing mutants or variants thereof.

8. A preparation having an arylacylamidase activity, obtained from a culture of the strain *Rhodococcus erythropolis* NCIB 12273 or aryl acylamidase-producing mutants or variants thereof.

9. A preparation as claimed in claim 8, containing a thiol protecting agent.

10. A method according to claim 9, in which an electrode poised at a suitable potential is contacted with a free-of-charge-transferring mediator compound and system comprising:

(a) a sample suspected to contain an N-acylated primary aromatic amine such as paracetomol or a derivative thereof, and (b) an enzyme capable of catalysing the hydrolysis of an N-acylated primary aromatic amine or a derivative thereof, the current flowing in the electrode being a measure of the quantity of hydrolysis products formed and thereby of the concentration of N-acylated primary aromatic amine or derivatives thereof in the sample.

* * * * *